US00PP24553P3

(12) United States Plant Patent
Lee

(10) Patent No.: US PP24,553 P3
(45) Date of Patent: Jun. 17, 2014

(54) ***SPIREA* PLANT NAMED 'BL0601'**

(50) Latin Name: *Spirea bumalda*
Varietal Denomination: BL0601

(75) Inventor: Robert Lee, Independence, LA (US)

(73) Assignee: Plant Development Services, Inc., Loxley, AL (US)

( * ) Notice: Subject to any disclaimer, the term of this patent is extended or adjusted under 35 U.S.C. 154(b) by 109 days.

(21) Appl. No.: 13/507,692

(22) Filed: Jul. 20, 2012

(65) Prior Publication Data

US 2014/0026267 P1 Jan. 23, 2014

(51) Int. Cl.
*A01H 5/00* (2006.01)

(52) U.S. Cl.
USPC ..... Plt./226

(58) Field of Classification Search
None
See application file for complete search history.

*Primary Examiner* — Wendy C Haas
(74) *Attorney, Agent, or Firm* — Cassandra Bright

(57) ABSTRACT

A new and distinct *Spirea* cultivar named 'BL0601' is disclosed, characterized by distinctive green foliage with a greyed-purple cast, change to red-orange in the fall. Plants are compact, sporadically bloom throughout the growing season and show an increased tolerance for foliar diseases. The new cultivar is a *Spirea,* suitable for ornamental garden purposes.

1 Drawing Sheet

Latin name of the genus and species: *Spirea bumalda.*
Variety denomination: 'BL0601'.

BACKGROUND OF THE INVENTION

The new cultivar is a product of a planned breeding program. Seeds collected by the inventor, Robert Lee, were planted and seedlings observed for interesting horticultural variations. Actual parentage is unknown, as the collected seeds were the result of open pollination of various *Spirea buldama* varieties.

The new variety was selected by the inventor and first propagated by softwood cuttings at a commercial nursery in Independence, La. The initial propagation showed the mutation to be stable and additional generations were propagated, also by softwood cuttings. Multiple generations have been reproduced since approximately May 2004, and have shown that the unique features of this cultivar are stable and reproduced true to type.

SUMMARY OF THE INVENTION

The cultivar 'BL0601' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BL0601' These characteristics in combination distinguish 'BL0601' as a new and distinct *Spirea* cultivar:

1. Green foliage with a greyed-purple cast that persists during the growing season.
2. Compact growth habit
3. Red-orange fall foliage color
4. Increased tolerance for foliar diseases.
5. Repeat sporadic blooming throughout the growing season.

COMPARISON TO PARENT VARIETY

Parent varieties are unknown.

COMMERCIAL COMPARISON

'BL0601' can be compared to the commercial variety *Spirea bumalda* 'Anthony Waterer' (unpatented). Plants of the new cultivar 'BL0601' are similar to plants of 'Anthony Waterer' in most horticultural characteristics, however, plants of the new cultivar 'BL0601' produce foliage with a distinctive greyed-purple cast not found on 'Anthony Waterer'. Additionally, the mature plant height of the new variety is approximately two to three feet, whereas mature plants of 'Anthony Waterer' are typically three to six feet tall. Flower color of 'BL0601' is significantly lighter than 'Anthony Waterer'.

'BL0601' can also be compared to the commercial variety *Spirea bumalda* 'Galen' U.S. Plant Pat. No. 21,712. Plants of the new cultivar 'BL0601' are similar to plants of this comparator in most horticultural characteristics, however, plants of the new cultivar 'BL0601' have foliage that emerges and maintains a green with greyed-purple tones, and changes to red-orange in the Fall, whereas 'Galen' has foliage that starts brownish-red, matures to green, and stays green in the Fall. Additionally, plants of 'BL0601' are overall larger and better resistant to heat than this comparator.

BRIEF DESCRIPTION OF THE PHOTOGRAPH

The accompanying photograph in FIG. 1 illustrates in full color a typical plant of 'BL0601' grown outdoors in Alabama. The plant is approximately 2 years old, and is shown in a three gallon container.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'BL0601' plants grown outdoors in Loxley, Ala. Plants are approximately 3 years old, in a 3 gallon nursery container. Measurements and numerical values represent averages of typical plant types.

Botanical classification: *Spirea bumalda* 'BL0601'.

PROPAGATION

Time to initiate rooting: Approximately 15 days at approximately 22° C. from softwood cuttings.

Root description: Fine, fibrous young roots, well branched.

PLANT

Growth habit: Compact shrub. Dense. Slow to moderate growth rate.

Height: Approximately 35 cm.

Plant spread: Approximately 72 cm.

Branching characteristics: Well branched, approximately 20 primary branches from center of plant, angled approximately 45°. Each primary branches has 4 to 6 lateral branches.

Primary branches:

- *Length of primary branches.*—Approximately 20 to 35 cm.
- *Diameter of primary branches.*—Approximately 0.4 cm.
- *Primary branch strength.*—Very strong, average flexibility, not brittle.
- *Primary branch color.*—Near RHS Greyed-Purple 183B.
- *Primary branch texture.*—Mostly smooth. Irregular steaks of cracking of bark, showing coloration underneath near Green 143C.

Lateral branches:

- *Length of lateral branches.*—Approximately 9 to 15 cm.
- *Number of lateral branches.*—Approximately 4 to 6 main lateral branches per primary branch.
- *Diameter of lateral branches.*—Average 0.25 cm.
- *Lateral branch strength.*—Very strong, flexible.
- *Lateral branch color.*—Near RHS Greyed-Purple N86C, wide streaks Greyed-Orange 175B.
- *Lateral branch texture.*—Smooth.
- *Number of leaves per lateral branch.*—Average 12.
- *Internode length.*—Average 0.8 cm.

Age of plant described: Approximately 2 years.

FOLIAGE

Leaf:

- *Type.*—Simple.
- *Arrangement.*—Alternate.
- *Average length.*—Approximately 3.5 cm.
- *Average width.*—Approximately 1.6 cm.
- *Shape of blade.*—Oval.
- *Apex.*—Acute.
- *Base.*—Broad attenuate.
- *Attachment.*—Stalked.
- *Margin.*—Crenate.
- *Texture of top surface.*—Glabrous.
- *Texture of bottom surface.*—Glabrous.
- *Foliage scent.*—None.
- *Color.*—Young foliage upper side: Near RHS Greyed-Purple N186B. Young foliage under side: Near RHS Green 137B, heavily flushed Greyed-Purple N186C. Mature foliage upper side: Near RHS Green 137A. Mature foliage under side: Near RHS Green 138A.
- *Venation.*—Type: Pinnate. Venation color upper side: Near RHS Yellow-Green 144B. Venation color under side: Near RHS Yellow-Green 144C.
- *Petiole.*—Length: About 0.3 cm. Diameter: About 0.15 cm. Color: Near RHS Yellow-Green 144B.

FLOWER

Bloom period:

- *Natural season.*—Late Spring.

Flower:

- *Arrangement.*—Umbellate corymbs of rotate flowers.

Inflorescence:

- *Diameter.*—Approximately 7.0 cm.
- *Height.*—Approximately 5.0 cm.

Peduncle:

- *Length.*—Average 2.3 cm.
- *Diameter.*—0.2 cm.
- *Color.*—Near RHS Yellow-Green 145B, flushed with Greyed-Purple 183D.
- *Texture.*—Finely pubescent.
- *Aspect.*—Straight to very slightly curved, approximately 35° angle from stem.

Flowers:

- *Depth.*—Average 0.3 cm.
- *Diameter.*—Average 0.6 cm.
- *Facing direction.*—Outwardly and upwardly facing.
- *Persistent or self-cleaning.*—Petals self cleaning, calyx persistent.
- *Fragrance.*—Faint.

Petals:

- *Length.*—Approximately 0.45 cm.
- *Width.*—Approximately 0.3 cm.
- *Apex*—Broadly acute.
- *Shape of petal.*—Obovate.
- *Petal margin.*—Entire.
- *Petal arrangement.*—Rotate.
- *Petal number.*—5.
- *Petal texture.*—Smooth.
- *Color.*—Upper surface at first opening: Near RHS Red-Purple 70A. Under surface at first opening: Near RHS Red-Purple 70B. Upper surface at maturity: Near RHS Red-Purple 70A. Under surface at maturity: Near RHS Red-Purple 70B. Upper surface at fading: Near RHS Red-Purple N74C. Under surface at fading: Near RHS Purple 77C.

Bud:

- *Shape.*—Dome.
- *Length.*—0.3 cm.
- *Diameter.*—0.4 cm.
- *Color.*—Near RHS Red-Purple 70A.

Calyx/sepals:

- *Quantity per flower.*—5 sepals.
- *Shape.*—Deltate.
- *Length.*—0.2 cm.
- *Width.*—0.3 cm.
- *Apex.*—Acute.
- *Base.*—Fused.
- *Margin.*—Entire.
- *Texture.*—Smooth.

*Color.*—Upper Surface: Near RHS Green 137B, tip Greyed-Purple N186B. Lower Surface: Near RHS Green 137B, tip Greyed-Purple N186C.

Pedicel:

*Length.*—0.2 cm.

*Diameter.*—0.1 cm.

*Color.*—Near RHS Green 138A, faintly flushed Greyed-Purple N186C.

*Texture.*—Softly pubescent.

*Color.*—Upper Surface: Near RHS Yellow-Green 145B with a flush of Greyed-Purple 185C. Lower Surface: Near RHS Yellow-Green 145B with a flush along margins of Greyed-Purple 185C.

REPRODUCTIVE ORGANS

Stamens:

*Number.*—5.

*Length.*—0.4 cm, protruding prominently from flower.

*Width.*—0.1 cm.

*Color.*—Near RHS Greyed-Purple N186B.

*Anthers.*—Length: Approximately 0.15 cm. Color: Near RHS Greyed-Purple N186A. Pollen: Moderate amount observed.

Pistil:

*Number.*—5.

*Length.*—0.35 cm.

*Style.*—Length: 0.2 cm. Color: Near RHS Red-Purple 71C.

*Stigma.*—Linear, colored near Red-Purple 71D.

OTHER CHARACTERISTICS

Disease and pest resistance: Not observed to be susceptible nor resistant to normal diseases and pests of *Spirea bumalda.*

Temperature tolerance: USDA Zone 6.

Fruit/seed production: Dry, follicle fruit. Approximately 0.2 cm in length, 0.15 cm wide. Colored near Grey-Brown N199C. Seeds dustlike.

What is claimed is:

1. A new and distinct cultivar of *Spirea* plant named 'BL0601' as herein illustrated and described.

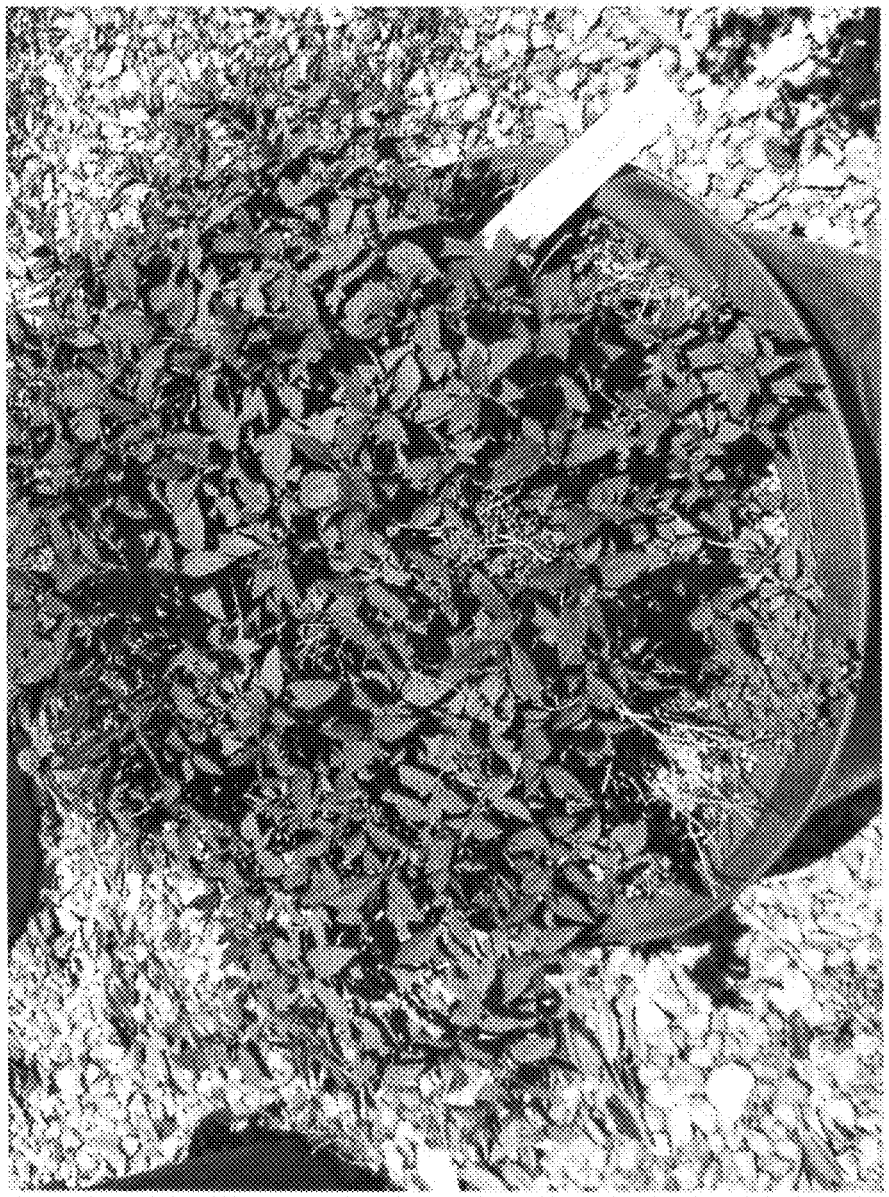

* * * * *